(12) United States Patent
Ariav et al.

(10) Patent No.: US 7,710,124 B2
(45) Date of Patent: May 4, 2010

(54) METHOD AND APPARATUS FOR DETECTING PANEL CONDITIONS

(75) Inventors: Arie Ariav, Doar-Na Hof Ashkelon (IL); Vladimir Ravitch, Ashkelon (IL); David Nitsan, Azur (IL)

(73) Assignee: Nexense Ltd., Yavne (IL)

( * ) Notice: Subject to any disclaimer, the term of this patent is extended or adjusted under 35 U.S.C. 154(b) by 525 days.

(21) Appl. No.: 10/589,191

(22) PCT Filed: Feb. 8, 2005

(86) PCT No.: PCT/IL2005/000155

§ 371 (c)(1),
(2), (4) Date: Sep. 25, 2007

(87) PCT Pub. No.: WO2005/076727

PCT Pub. Date: Aug. 25, 2005

(65) Prior Publication Data

US 2008/0110262 A1    May 15, 2008

(30) Foreign Application Priority Data

Feb. 12, 2004   (IL) .................................. 160365

(51) Int. Cl.
*G01R 27/04* (2006.01)

(52) U.S. Cl. .............. 324/637; 324/71.1; 73/624; 73/632; 73/597

(58) Field of Classification Search ............... 324/637, 324/71.1, 76.11; 73/597, 624, 632
See application file for complete search history.

(56) References Cited

U.S. PATENT DOCUMENTS 3,771,568 A * 11/1973 Bischoff et al. .............. 137/805
5,271,267 A * 12/1993 Baumoel ................... 73/54.41
6,244,743 B1    6/2001 Bååth
6,480,141 B1   11/2002 Toth et al.

\* cited by examiner

*Primary Examiner*—Vincent Q Nguyen

(57) ABSTRACT

A method and apparatus for detecting a predetermined condition of a panel by transmitting a cyclically-repeating energy wave through the material (41) of the panel from first location (43*a*) to a second location (43*b*); measuring the transit time of the cyclically-repeating energy wave from the first location to the second location; and utilizing the measured transit time to detect the predetermined condition including the force on, the temperature of, a deformation in, the fatigue condition of, or a fracture in, structural panel, the presence of a force applied to, water on, or breakage in of the panel.

18 Claims, 3 Drawing Sheets

METHOD AND APPARATUS FOR DETECTING PANEL CONDITIONS

RELATED APPLICATION

This application is a National Phase Application of PCT Application No. PCT/IL2005/000155 having International Filing Date of Feb. 8, 2005, which claims priority from Israel Patent Application No. 160365, filed on Feb. 12, 2004. The contents of the above Applications are all incorporated herein by reference.

FIELD AND BACKGROUND OF THE INVENTION

The present application relates to a method and to an apparatus for detecting various panel conditions. Examples of such panel conditions described below includes various physical conditions of a structural panel such as an aircraft wing; various conditions of a window panel; the presence or absence of an object on a floor panel (e.g., in a space monitor); and the presence and location of pressure applied (e.g., by a stylus) to a touch panel.

The present application is related to: International Application PCT/IL00/00241 published Nov. 9, 2000 as International Publication No. WO 00/67013; International Application PCT/IL02/00854 filed Oct. 24, 2002, Published May 1, 2003 as International Publication No. WO 03/036321; International Application PCT/IL02/00983, filed Dec. 5, 2002, published Jun. 12, 2003 as International Publication No. WO 03/048668; and U.S. Pat. No. 6,621,278 issued Sep. 16, 2003, the contents of which applications and patent are incorporated herein by reference in their entirety.

The above-cited applications and patent relate to methods and apparatus for measuring, with extremely high sensitivity, various parameters having a known or determinable relationship with respect to the transit time of an energy wave (electromagnet or sonic) through a medium (solid, liquid or gas). Briefly, this is done by transmitting through the medium a cyclically-repeating energy wave; receiving the energy wave transmitted through the medium; detecting a predetermined fiducial point in the received energy wave; continuously changing the frequency of the transmission of the energy wave in accordance with the detected fiducial point of each received energy wave such that the number of waves received is a whole integer; and measuring the changes in frequency to produce a measurement of changes in transit time of the energy wave from the transmitter to the receiver, and thereby a measurement of the predetermined parameter.

The above-cited applications and patent described many implementations of such method and apparatus in many fields, both medical and non-medical, for detecting or measuring various conditions with an extremely high degree of sensitivity.

OBJECTS AND BRIEF SUMMARY OF THE PRESENT INVENTION

An object of the present invention is to provide additional applications of the method and apparatus described in the above-cited applications and patents, particularly for detecting or measuring various conditions relating to panels, such as various physical conditions of aircraft wings or other structural panels, the condition of window panels, the presence of an object in a floor panel (e.g., space monitoring), and the entry of information on a touch panel. Another object of the present invention is to provide a method and apparatus for detecting, with an extremely high degree of sensitivity, various conditions of panels, such as those referred to above.

According to a broad aspect of the present invention, there is provided a method of detecting a predetermined condition of a panel, comprising: transmitting a cyclically-repeating energy wave through a transmission channel in said panel consisting solely of the material of the panel; measuring the transit time of the cyclically-repeating energy wave from the first location to the second location; and utilizing the measured transit time to detect the predetermined condition of the panel.

A number of embodiments of the invention are described below for purposes of example.

According to one described preferred embodiment, the panel is a structural panel, such as an aircraft wing, and the condition to be detected is a force on, the temperature of, a deformation in, the fatigue condition of, or a fracture in the structural panel. According to another described embodiment, the panel is a window panel, and the condition to be detected is the presence or absence of a force applied to the window panel, water on the window panel, or a breakage of the window panel.

According to a further described embodiment, the panel is a floor, and the condition to be detected is the presence or absence of an object on the floor, as well as (in one described embodiment) the movement of the object over the floor. Such an application is particularly useful as a space monitor to monitor against intrusions.

A further embodiment of the invention is described wherein the panel is a touch panel, and the condition to be detected is the presence or absence of pressure applied to the touch panel. In a particular embodiment of the latter application, the cyclically-repeating energy wave is transmitted through at least two separate energy wave transmission channels in the touch panel, and the transit time through each of the energy wave transmission channels is measured such that the location of the application of the pressure (e.g., by a user's finger or by a stylus) to the touch panel can be determined by triangulation.

In all the described preferred embodiments, the transit time of the cyclically-repeating energy wave from the first location to the second location is measured according to the method described in the above-cited U.S. Pat. No. 6,621,278, e.g., by: detecting a predetermined fiducial point in the cyclically-repeating energy wave received at the second location; continuously changing the frequency of transmission of the cyclically-repeating energy wave in accordance with the detected fiducial point of each received wave such that the number of waves received is a whole integer; and utilizing the measured change in frequency to produce a measurement of the transit time of the cyclically-repeating energy wave from the first location to the second location.

In all of the described preferred embodiments, the cyclically-repeating energy wave is an acoustical wave, although it will be appreciated that the invention could also be implemented with electromagnetic waves, such as visible light, infra-red, or RF, particularly where the modulation and delay features described in the above-cited U.S. Pat. No. 6,621,278 are used.

Further features and advantages of the invention will be apparent from the description below.

BRIEF DESCRIPTION OF THE DRAWINGS

The invention is herein described, by way of example only, with reference to the accompanying drawings, wherein.

It is to be understood that the foregoing drawings, and the description below, are provided primarily for purposes of facilitating understanding the conceptual aspects of the invention and various possible embodiments thereof, including what is presently considered to be a preferred embodiment. In the interest of clarity and brevity, no attempt is made to provide more details than necessary to enable one skilled in the art, using routine skill and design, to understand and practice the described invention. It is to be further understood that the embodiments described are for purposes of example only, and that the invention is capable of being embodied in other forms and applications than described herein.

DESCRIPTION OF PREFERRED EMBODIMENTS

Figure 1:
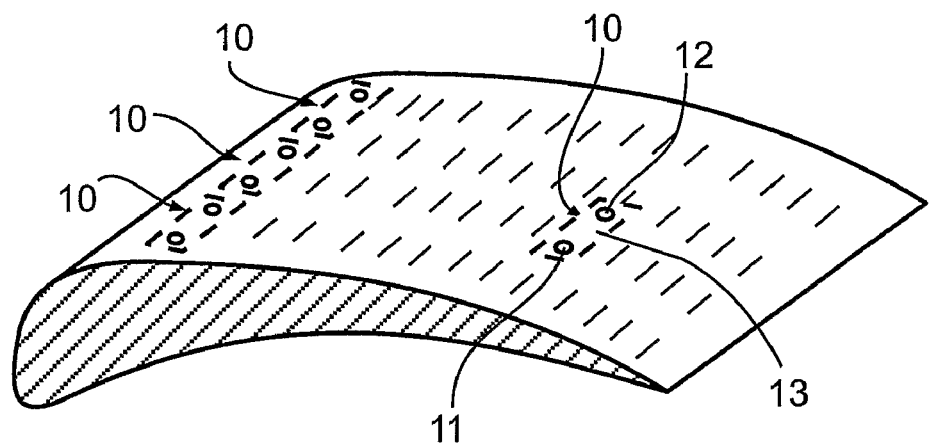
FIG. 1 illustrates a structural panel, in the form of an airplane wing, constructed in accordance with the present invention for detecting various physical conditions, such as the distribution of forces on, or temperature in the wing, deformations in the wing, a fatigue condition of the wing, and/or a fracture in the wing.

FIG. 1 illustrates the invention implemented in a structural panel, more particularly an aircraft wing 2, for detecting any one of various physical conditions of the wing which affects the transit time of a sonic wave through the material of the wing. Among the conditions that may be detected in this manner are pressure and/or temperature distribution of the wing, deformations in the wing, a fatigue condition in the wing material, or a fracture in the wing.

For this purpose, the wing 2 is provided with a plurality of sensors 10 arrayed as desired on the wing in order to sense the condition of the wing at a plurality of regions thereon. Each sensor includes a sonic transmitter 11 and a sonic receiver 12 spaced from the transmitter to define, between them, an acoustical channel 13 constituted of the material of the wing itself. As described more particularly with respect to FIG. 2, a cyclically-repeating sonic wave is transmitted from the transmitter 11 through the portion of the wing serving as the respective acoustical channel to the receiver 12. The transit time of the sonic wave through the respective acoustical channel is measured in the respective sensor 10, and is utilized to detect the predetermined condition, e.g., deformation of, or temperature in, the respective region of the wing, a fracture or fatigue condition in the wing, etc., any of which conditions affects the transit time of the sonic wave through the respective acoustical channel, from the respective transmitter to the respective receiver.

Figure 2:
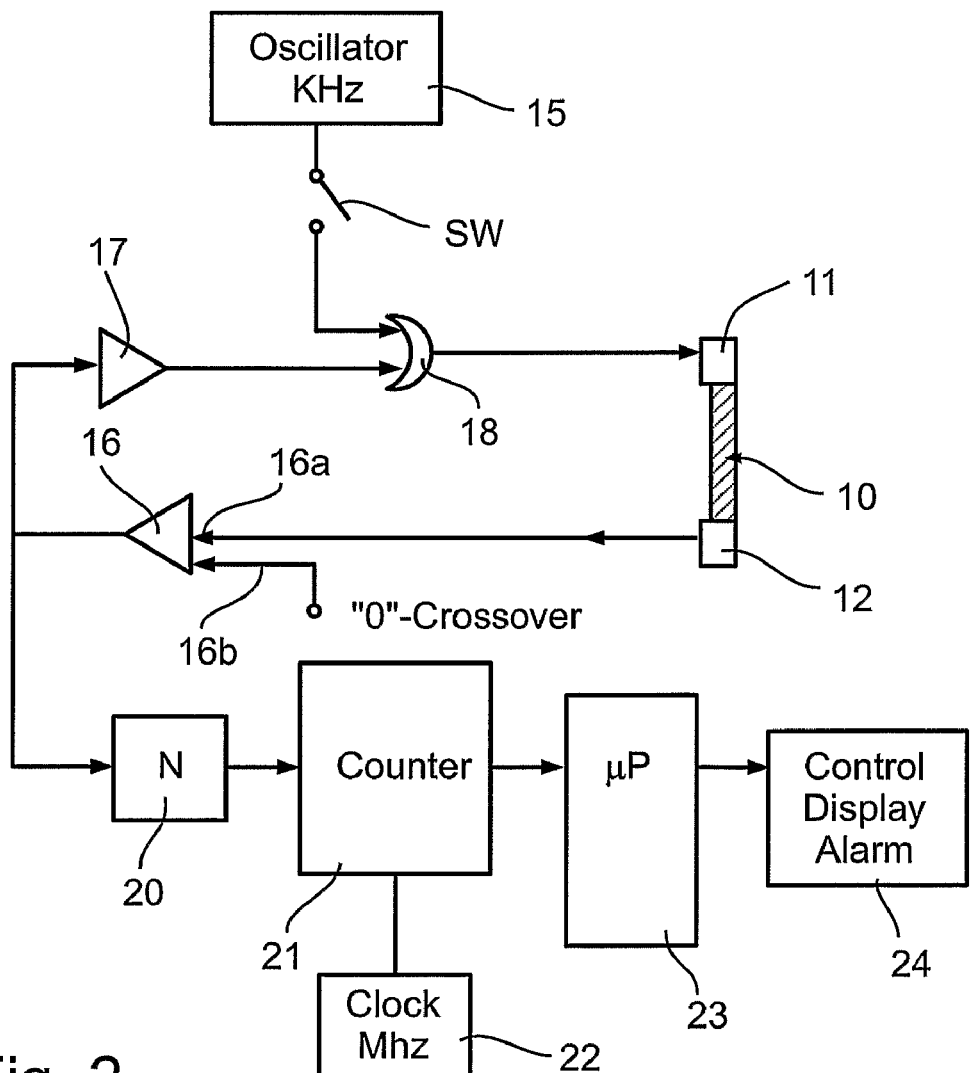
FIG. 2 is a block diagram illustrating the control and processing circuitry for detecting the predetermined condition in the structural panel of FIG. 1.

FIG. 2 illustrates the measuring circuit of each sensor 10 for measuring the transit time of the sonic wave from its respective transmitter 11 to its respective receiver 12. As more particularly described in the above-cited International patent applications and U.S. patent, such circuit is constructed and operates as follows:

Initially, oscillator 15 is energized while switch SW is closed so as to cause transmitter 11 to transmit a succession of sonic pulses until such pulses are received by receiver 12. Once the pulses are received by receiver 12, switch SW is opened so that the pulses received by receiver 12 are thereafter used for controlling the transmitter 11.

The sonic signals received by receiver 11 are fed to a comparator 16 via its input 16a. Comparator 16 includes a second input 16b connected to a predetermined bias so as to detect a predetermined fiducial in the received signal. In the example illustrated in FIG. 2, this predetermined fiducial point is the "zero" cross-over point of the received signal; therefore, input 16b of comparator 16 is at a zero bias.

The output of comparator 16 is fed to an amplifier 17, which is triggered to produce an output signal at each fiducial point (zero cross-over point) in the signals received by receiver 12. The outputs from amplifier 17 are fed via an OR-gate 18 to trigger the transmitter 11 for the next sonic pulse. Since switch SW is open, transmitter 11 will thus be triggered by each signal received by the receiver 12 to transmit the next sonic pulse in the succession of pulses.

It will thus be seen that the frequency of the output pulses or signals from transmitter 12 will change with a change in the transit distance, i.e., the spacing between the transmitter 11 and receiver 12. It will also be seen that the number of wavelengths or pulses in the signal transmitted by transmitter 11 and received by receiver 12 will be a whole integer. This change in frequency by the transmitter 11, while maintaining the number of waves between the transmitter and receiver 12 as a whole integer, enables a precise determination to be made of the transit distance, i.e., the distance between the transmitter and receiver.

A summing circuitry, including counters 20 and 21, clock 22 and microprocessor 23, enables the detected frequency difference, and thereby the measurement precision, to be increased by a factor "N", such that the precision of the measurement can be preset, almost without limitation, by the selection of the appropriate frequency, clock rate for clock 22, and summation factor "N" for counter 20. As further shown in FIG. 2, the output from microprocessor 23 may be used for display, alarm and/or control purposes, as schematically shown at 24.

Further details of the construction and operation of such an apparatus are available from the above-cited International Applications and U.S. Pat. No. 6,621,278, incorporated herein by reference. For example, U.S. Pat. No. 6,621,278 includes a modulation feature, and also a delay line feature, which features significantly extend the possible applications of such apparatus for measuring various types of parameters.

Figure 3:
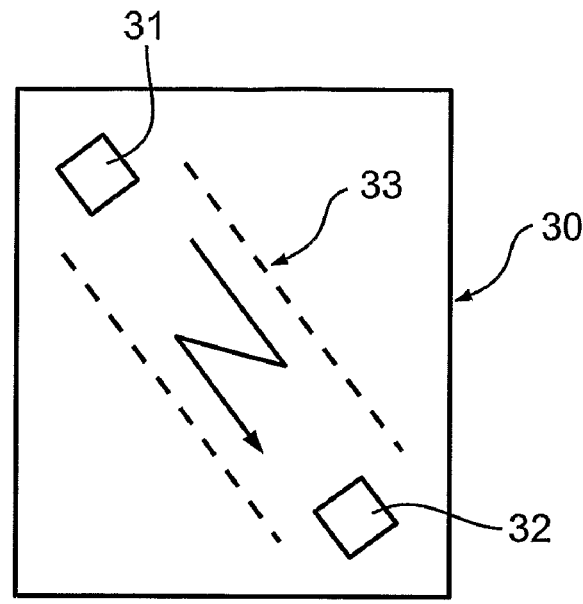
FIG. 3 illustrates the invention applied to a window panel in order detect the presence of a force applied to, or a breakage of, the window panel (e.g., an attempted forced entry), or the presence of water on the window panel (e.g., to actuate the wiper blades)

FIG. 3 illustrates the invention implemented in a window panel for detecting any one of a number of conditions affecting the transit time of a sonic wave moving through an acoustical channel in the window. Thus, as shown in FIG. 3, the window, therein generally designated 30, includes a sonic transmitter 31 at one end, and a sonic receiver 32 at the opposite end so as to define an acoustical channel 33 between them constituted of the material of the window itself. Should a pressure be applied against the window, the acoustical channel 33 will be deformed (lengthened), thereby changing the transit time of the sonic wave from the transmitter to the receiver. This transit time will also be changed if the window should be broken, or if the window is wetted, e.g., by rain. Accordingly, any one of the above conditions can be sensed by measuring the transit time, e.g., using the circuit of FIG. 2, of the sonic waves from the transmitter 31 to the receiver 32.

Figure 4:
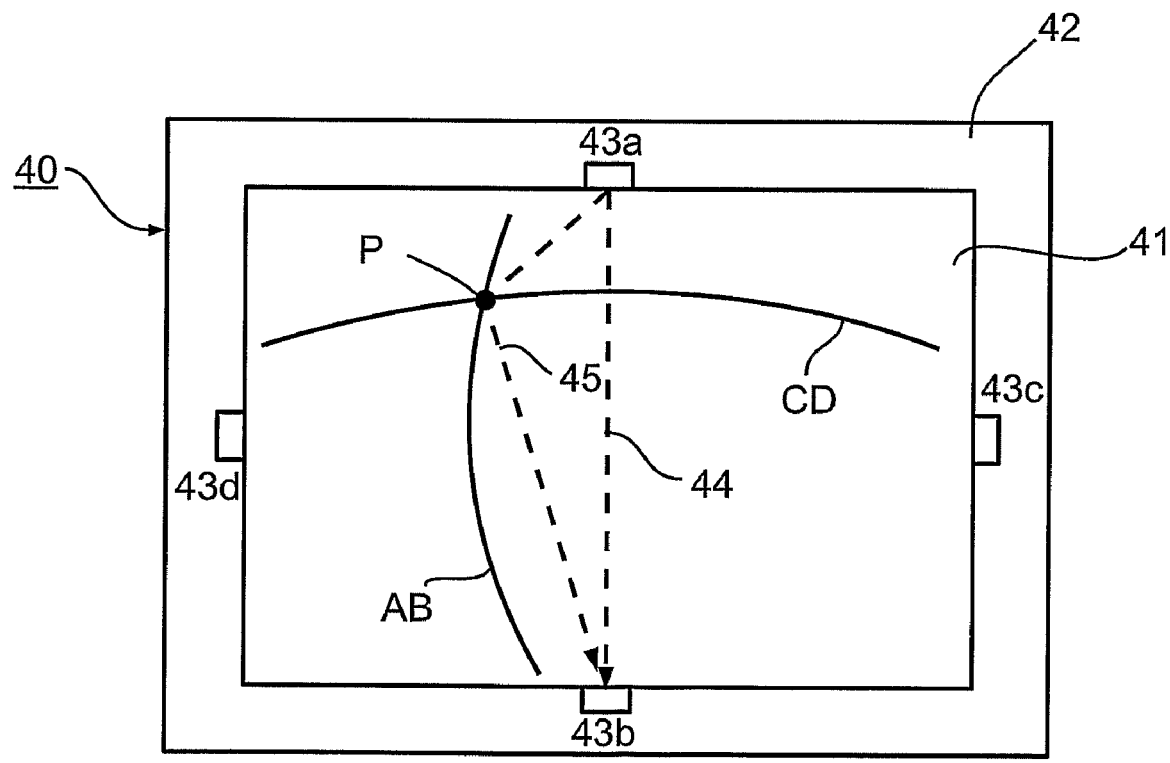
FIG. 4 illustrates a touch-screen type panel constructed in accordance with the present invention for determining the presence and location of pressure points as applied to the touch screen, e.g., by the user's finger, a stylus, etc.

FIG. 4 illustrates the invention implemented in a touch-screen type panel, to indicate not only that a particular point on the screen has been touched, but also the location of the touched point. Such devices are widely used to combine a display and an input keyboard in one unit.

One known type of touch screen includes two transparent resistor layers separated by insulating spacers. A voltage is applied across one resistor layer, and the voltage across the second resistor layer is measured, such that the ratio between the applied and measured voltages marks the location of the point touched on the screen. Such known devices, however, are quickly worn out. Another known type of touch screen includes a special pen which is moved to change its distance between a sonic transmitter and a sonic receiver attached to the screen. In such device, however, the sonic waves propagate through air, and therefore the environmental conditions (motion of air, temperature, position of user arm, etc.) may result in considerable errors. In addition, such known devices require the use of a special pen.

A touch screen constructed in accordance with the present invention, as illustrated in FIG. 4, avoids many of the foregoing disadvantages.

The touch screen illustrated in FIG. 4, therein generally designated 40, includes a glass panel 41 and an underlying layer 42 of a damper or sound-absorbing material, such as rubber. Four ultrasound transducers 43*a*-43*d* are located on the four outer edges of the glass panel 41 and are underlined by the sound absorbing layer 42. Each of the sonic transducers 43*a*-43*d* is capable of transmitting and receiving sonic waves propagated through the glass panel 41.

The four transducers may be organized in at least two, and preferably six, pairs of transmitters/receivers which work alternately. Thus, when the user does not touch the glass surface, the ultrasound wave propagates directly from the transmitter of the pair to the receiver of the pair as shown by line 44. Since there is no reflection from the glass borders, the frequency depends just on the known distance between the transmitter and receiver and the known ultrasound velocity.

However, when a point on the glass panel is touched, e.g., by the user's finger or by a stylus, there is a point of reflection as shown by line 45, which generates an additional wave having a length depending on the position of the touch point P. Thus, the phase of the received wave will be changed thereby changing the fiducial point used to trigger the next sonic pulse, such that the number of waves received by the respective receiver will be a whole integer. It will thus be seen that the frequency shift depends on the position of the touch point P.

Theoretically two acoustical channels through the glass plate 41 will define the touch point by triangulation. For example, assuming that transducers 43*a* and 43*b* define one acoustical channel, line AB will define a line of equal frequency for that respective channel; and assuming transducers 43*c* and 43*d* define a second acoustical channel, line CD define a second line of equal frequency for that channel. Accordingly, the actual location of the touch point, shown at P in FIG. 4, will be the intersection of lines AB and CD.

While two acoustical channels, therefore, are all that is necessary, a higher degree of accuracy is attainable when more than two acoustical channels are used. As one example, six acoustical channels may be used constituted of the following ultrasonic pairs: 43*a*-43*b*; 43*c*-43*d*; 43*a*-43*c*; 43*d*-43*b*; 43*a*-43*d*; and 43*b*-43*c*.

Figure 5:
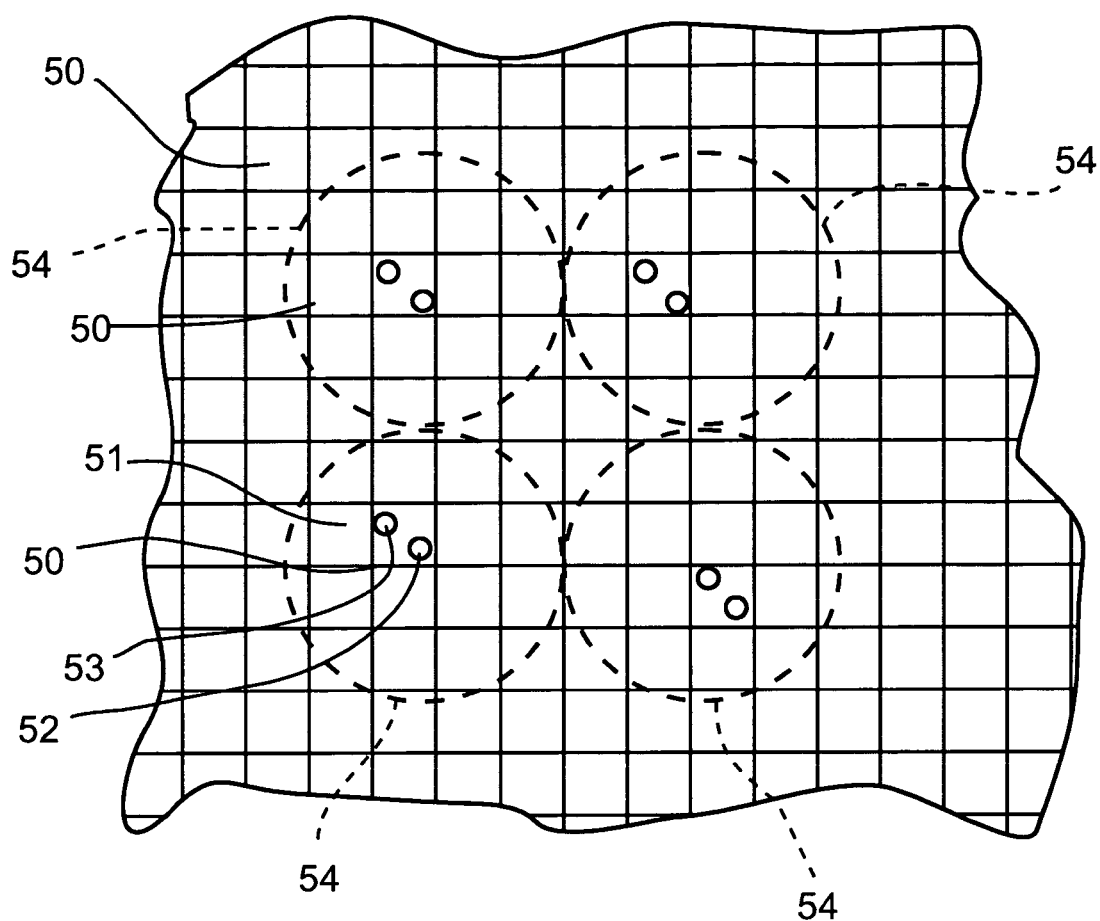
FIG. 5 illustrates the invention embodied in a floor to detect the presence and/or movement of an object over the floor, e.g., for use as a space monitor to prevent unauthorized intrusions.

FIG. 5 illustrates the invention embodied in a space monitor or the like for detecting the presence or entry of an object onto a floor. For this purpose, the floor is constituted of a plurality of floor tiles 50, some of which are constructed with a sonic transmitter 51 at on end and a sonic receiver 52 at the opposite end, to define an acoustical channel 53 between them. Each such tile so constructed thus defines a force sensor which senses the presence or entry of an object onto the respective tile.

Figure 6:
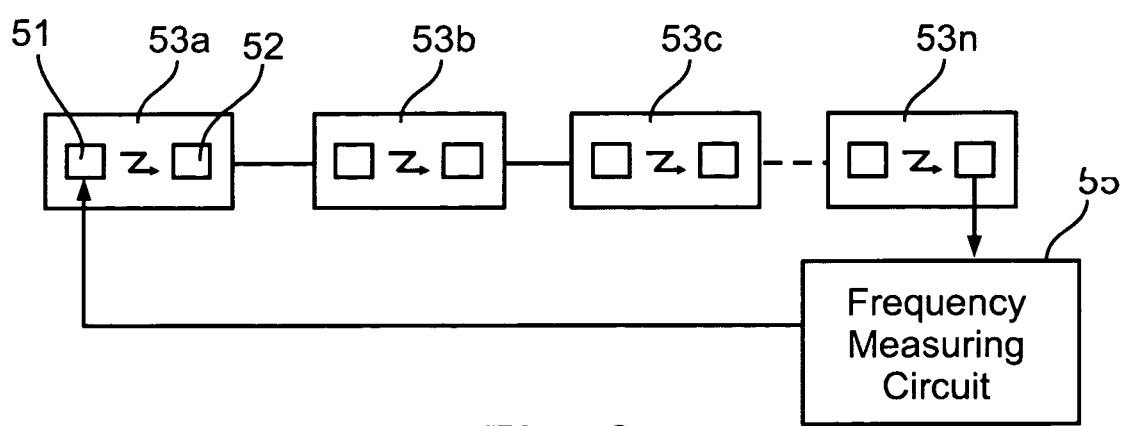
FIG. 6 illustrates an example of a closed-loop circuit connection of the various sensors in the floor monitor of FIG. 5 to enable a common measuring circuit to be used for all the sensors.

In the embodiment illustrated in FIG. 5, a plurality of tiles are so constructed to serve as force sensors for sensing an object thereon, as schematically indicated by broken lines 54. FIG. 6 illustrates one manner of connecting a plurality of such acoustical channels, therein designated 53*a*-53*n*, into a closed loop such that the receipt of a sonic wave by the receiver in one channel triggers the transmission of the sonic wave in the next channel of the loop. In the illustrated arrangement, a common frequency measuring circuit 55 is connected within the loop, so that the total transit times of all the channels are used to detect the presence or entry of an object onto the floor panels.

The closed-loop arrangement illustrated in FIG. 6 thus enables a single frequency measuring circuit 54 to be used for monitoring the space defined by the floor panels 51 constructed as force sensors in the manner described above. Thus, such a circuit is capable only of detecting the entry of an object 54 into the monitored space. If desired, the individual force-sensor tiles could be sequentially scanned to feed the common frequency measuring circuit 55, such as to enable detection of the movement of the object within the space defined by the force-sensor tiles.

While the invention has been described with respect to several preferred embodiments, it will be appreciated that these are set forth merely for purposes of example, and that many other applications of the invention may be made. For example, the invention may be used to detect the condition of other types of structural members, e.g., in building structures, bridge structures, etc. Many other variations and applications of the invention will be apparent.

What is claimed is:

1. A method of detecting a predetermined condition of a panel, comprising:

transmitting a cyclically-repeating energy wave through a transmission channel in said panel consisting solely of the material of said panel;

measuring the transit time of said cyclically-repeating energy wave from said first location to said second location;

and utilizing said measured transit time to detect said predetermined condition of the panel;

wherein said panel is a structural panel, and said condition to be detected is a force on, the temperature of, a deformation in, the fatigue condition of, or a fracture in said structural panel.

2. The method according to claim 1, wherein said panel is a window panel, and said condition to be detected is the presence or absence of a force applied to said window panel, water on the window panel, or a breakage of the window panel.

3. The method according to claim 1, wherein said panel is a floor, and said condition to be detected is the presence or absence of an object on said floor.

4. The method according to claim 3, wherein said floor is constituted of a plurality of floor tiles; and a said cyclically-variable energy wave is transmitted through each of a plurality of said floor tiles such that each such floor tile defines an energy wave transmission channel therethrough; the transit time through each of said energy wave transmission channels being measured to thereby detect the movement of the object over said floor panel.

5. The method according to claim 3, wherein said floor is constituted of a plurality of floor tiles; and a said cyclically-variable energy wave is transmitted through each of a plurality of said floor tiles such that each floor tile defines an energy wave transmission channel therethrough; the total transit time of all said energy wave transmission channels being measured by a common measuring circuit to thereby detect the presence of an object on any of said floor tiles.

6. The method according to claim 1, wherein the transit time of said cyclically-repeating energy wave through said transmission channel is an acoustical wave and is measured by:
    transmitting an acoustical wave through said transmission channel from a first location of said panel to a second location of said panel;
    continuously changing the frequency of transmission of the acoustical wave such that the number of waves received at said second location is a whole integer;
    and utilizing the measured change in frequency to produce a measurement of said transit time of the acoustical wave from said first location to said second location.

7. The method according to claim 6, wherein said panel is a touch panel, and said condition to be detected is the presence or absence of pressure applied to said touch panel.

8. The method according to claim 7, wherein said acoustical wave is transmitted through at least two separate energy wave transmission channels in said touch panel, and a line of equal frequency through each of said transmission channels is determined and used to determine by triangulation the location of the application of pressure to said touch panel.

9. The method according to claim 6, wherein said panel includes a plurality of acoustical wave transmission channels each extending through a portion of the panel; each of said transmission channels including a transmitter and receiver; the transmitters and receivers being connected in a closed loop such that the receipt of an acoustical wave in one channel triggers the transmission of an acoustical wave in the next channel of the loop, whereby the total transit times of all the channels are used to detect the predetermined condition of said panel.

10. Apparatus for detecting a predetermined condition of a panel, comprising:
    a transmitter at a first location on said panel for transmitting a cyclically-repeating energy wave through a transmission channel in said panel and consisting solely of the material of said panel;
    a receiver at said second location on said panel for receiving said cyclically-repeating energy wave;
    and an electrical system designed for measuring the transit time of the cyclically-repeating energy wave through said transmission channel from said first location to said second location and for thereby producing an indication of the condition of the panel;
    wherein said panel is a structural panel, and said electrical system is designed to provide an indication of a force on, the temperature of, a deformation in, a fatigue condition of, or a fracture in the structural panel.

11. The apparatus according to claim 10, wherein said panel is a window panel, and said electrical system is designed to provide an indication of the presence or absence of a force applied to the window panel, water on the window panel, or a breakage of the window panel.

12. The apparatus according to claim 10, wherein said panel is a floor, and said electrical system is designed to provide an indication of the presence or absence of an object on said floor.

13. The apparatus according to claim 12, wherein said floor is constituted of a plurality of floor tiles, and wherein each of a plurality of said floor tiles includes a transmitter and receiver for transmitting a cyclically-repeating energy wave through an energy wave transmission channel therein; said electrical system being designed to measure the transit time of the energy wave through each of said energy wave transmission channels such as to detect movement of the object over said floor.

14. The apparatus according to claim 12, wherein said floor is constituted of a plurality of floor tiles; and said cyclically-variable energy wave is transmitted through each of a plurality of said floor tiles such that each such floor tile defines an energy wave transmission channel therethrough; the total transit time of all said energy wave transmission channels being measured by a common measuring circuit to thereby detect the presence of an object on any of said floor panels.

15. The apparatus according to claim 10, wherein said energy wave is an acoustical wave, and said electrical system measures the transit time of said acoustical wave from said first location to said second location by:
    continuously changing the frequency of transmission of the acoustical wave such that the number of waves received is a whole integer;
    and utilizing the measured change in frequency to produce a measurement of said transit time of the acoustical wave from said first location to said second location.

16. The apparatus according to claim 15, wherein said panel is a touch panel, and said electrical system is designed to detect the presence or absence of pressure applied to said touch panel.

17. The apparatus according to claim 15, wherein there are a plurality of transmitters and receivers defining a plurality of acoustical wave transmission channels at different locations and orientations through said touch panel; and wherein said electrical system is designed to determine a line of equal frequency through each of said acoustical wave transmission channels and to utilize said lines to determine by triangulation the location of the application of pressure to said touch panel.

18. The apparatus according to claim 15, wherein said panel includes a plurality of acoustical wave transmission channels each extending through a portion of the panel; each of said transmission channels including a said transmitter and receiver; the transmitters and receivers being connected in a closed loop such that the receipt of an acoustical wave in one channel triggers the transmission of an acoustical wave in the next channel of the loop, whereby the total transit times of all the channels are used to detect the predetermined condition of said panel.

* * * * *